United States Patent
Ceballos et al.

(10) Patent No.: US 12,083,214 B2
(45) Date of Patent: *Sep. 10, 2024

(54) HAIR-TREATMENT COMPOSITION AND METHODS OF USE

(71) Applicant: L'OREAL, Paris (FR)

(72) Inventors: Angellica Ceballos, Hackensack, NJ (US); Allison Chin, Hoboken, NJ (US); Anthony Potin, East Rutherford, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/393,929

(22) Filed: Aug. 4, 2021

(65) Prior Publication Data

US 2021/0361558 A1 Nov. 25, 2021

Related U.S. Application Data

(63) Continuation of application No. 15/665,189, filed on Jul. 31, 2017, now Pat. No. 11,090,256.

(51) Int. Cl.
| | | |
|---|---|---|
| *A61K 8/92* | (2006.01) | |
| *A61K 8/34* | (2006.01) | |
| *A61K 8/365* | (2006.01) | |
| *A61K 8/37* | (2006.01) | |
| *A61K 8/42* | (2006.01) | |
| *A61Q 5/00* | (2006.01) | |
| *A61Q 5/06* | (2006.01) | |

(52) U.S. Cl.
CPC .............. *A61K 8/922* (2013.01); *A61K 8/342* (2013.01); *A61K 8/365* (2013.01); *A61K 8/375* (2013.01); *A61K 8/42* (2013.01); *A61Q 5/002* (2013.01); *A61Q 5/06* (2013.01); *A61K 2800/26* (2013.01); *A61K 2800/34* (2013.01)

(58) Field of Classification Search
None
See application file for complete search history.

(56) References Cited

U.S. PATENT DOCUMENTS

| | | | |
|---|---|---|---|
| 4,820,511 | A | 4/1989 | Hoeffkes et al. |
| 2004/0106529 | A1 | 6/2004 | Fack et al. |
| 2007/0104676 | A1 | 5/2007 | Moser et al. |
| 2011/0256249 | A1 | 10/2011 | Campbell et al. |

FOREIGN PATENT DOCUMENTS

| | | |
|---|---|---|
| DE | 102011000927 A1 | 8/2012 |
| DE | 102012205083 A1 | 10/2013 |
| EP | 0278660 B1 | 10/1992 |
| WO | 98/40046 A2 | 9/1998 |

OTHER PUBLICATIONS

"ProCondition 22," Product Bulletin, 2011.
Tom Schoenberg, "Formulating Non-Traditional Hair Conditioners," 2007, pp. 1-5.

*Primary Examiner* — Nicole P Babson
(74) *Attorney, Agent, or Firm* — POLSINELLI PC

(57) ABSTRACT

The present disclosure relates to hair-treatment compositions, which are particularly useful for providing styling, hair manageability, hair care, and conditioning properties to hair. The hair-treatment compositions typically include: (a) about 1 to about 3 wt. % of one or more vegetable oils; (b) about 2 to about 4 wt. % of one or more solid fatty alcohols; (c) 1 wt. % or less of one or more nonionic surfactants; (d) one or more non-silicone shine enhancers; (e) one or more amidoamines: (f) one or more acids; and (g) water. The unique combination of ingredients results in a product having a milky appearance and a fluid viscosity. Kits comprising the hair-treatment compositions and methods of treating hair using the hair-treatment compositions are also disclosed.

16 Claims, 3 Drawing Sheets

HAIR-TREATMENT COMPOSITION AND METHODS OF USE

CROSS-REFERENCE TO RELATED APPLICATIONS

This application claims priority to and is a continuation of U.S. patent application Ser. No. 15/665,189, filed on Jul. 31, 2017, the entirety of which is herein incorporated by reference.

FIELD OF THE DISCLOSURE

The present disclosure relates to hair-treatment compositions, kits comprising the hair-treatment compositions, and methods for treating hair using the hair-treatment compositions.

BACKGROUND

Hair is cleansed and treated with many cosmetic regiments to improve its look, color, style, etc. These various regiments however can remove the hair's natural oils and impart structural damage to the hair. For instance, shampooing is used primarily to cleanse the. Shampoos are often formulated with anionic surfactants that primarily clean as opposed to condition the hair. Anionic surfactants are highly effective for removing dirt, pollution, build-up, etc., from the hair, but they also remove sebum, a naturally occurring oily or waxy matter that automatically lubricates hair.

Shampooing can therefore leave the hair with a dry or coarse texture. Furthermore, thoroughly cleansed hair can become extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing properties of dry hair remain poor, and the hair has undesirable electrostatic properties in a low humidity atmosphere that causes the hair to "fly away" thereby further reducing the brushing properties of the hair.

Chemical hair treatments can further eliminate hair's natural oils (e.g., sebum) and alter the hair fiber's chemical and physical properties. The process of permanently changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening (or bleaching), generally requires the use of harsh chemicals such as alkalizing chemicals. These chemicals cause the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

There are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While chemically treating hair can impart desirable cosmetic changes to the hair (e.g., change the color, shape, etc.) these chemical treatments can damage the hair fibers, in some cases even more than repeated shampooing of the hair. Like shampooing, chemical treatments can leave the hair dry with a course texture.

Conditioning compositions are used to improve or return to the hair its natural luster, shine, and softness, for example, after shampooing the hair and/or after subjecting the hair to a chemical treatment. Conditioning compositions are often applied as rinses, cream-like emulsions, or lotions, and typically include one or more cationic compound. When used with shampooing, the commonly accepted method for conditioning the hair has been to shampoo the hair, followed by rinsing the hair, and then applying a conditioner composition, followed by a second rinse. This improves the wet combing properties of the hair often because the conditioner composition coats the hair shaft and causes individual hair fibers in to resist tangling and matting because of the conditioner residue retained on the hair shaft.

SUMMARY OF THE DISCLOSURE

The present disclosure relates to compositions and methods for treating hair, in particular human hair of the head. The unique combination of ingredients in the compositions results in a final product having a milky appearance and a fluid viscosity, which can be applied to the hair, allowed to remain on the hair for a period of time, and rinsed from the hair. The hair-treatment compositions of the disclosure are particularly useful for providing styling and conditioning benefits to the hair, for example, imparting shine, color vibrancy, smoothness, softness, and discipline to the hair.

The hair-treatment compositions include natural ingredients such as vegetable-derived oils; synthetic materials, such as silicones are not required. Thus, the hair-treatment compositions may be natural products that do not include synthetic ingredients. Even without synthetic ingredients, such as silicones, the hair-treatment compositions are stable, have a fluid viscosity, and provide superior performance. In comparison to typical silicone-based products and other comparative formulations, the instant hair-treatment compositions provide better conditioning, smoothness, shape, shine, and discipline to hair with a cleaner, light-weight feel.

The hair-treatment compositions of the disclosure typically include:
  (a) about 1 to about 3 wt. % of one or more vegetable oils;
  (b) about 2 to about 4 wt. % of one or more solid fatty alcohols;
  (c) one or more nonionic surfactants;
  (d) one or more non-silicone shine enhancers;
  (e) one or more amidoamines:
  (f) one or more acids; and
  (g) water.

The hair-treatment compositions typically have a fluid viscosity, for example a viscosity of less than 30 DU (units of deflection) and may have a milky appearance (opaque appearance). A fluid viscosity and a milky appearance are desirable. The fluid viscosity allows the product to be easily administered from packaging, to quickly infiltrate the hair, and completely cover the hair fibers. Special means for expelling or administering the product from packaging is not necessary and application to the hair is efficient. The milky appearance results from the unique combination of typically natural ingredients that provide conditioning, nourishing, and styling benefits to the hair.

Additionally, the hair-treatment compositions typically have a low pH (e.g., less than 7, for instance, a pH of about 3 to about 5). Also, as mentioned above, the hair-treatment compositions do not require synthetic compounds including synthetic silicone compounds. Thus, the hair-treatment compositions may be free or essentially free of silicones.

Non-limiting examples of vegetable oils include coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof. In some cases, the hair-treatment composition includes at least coconut oil. Also useful is a combination of coconut oil and soybean oil.

Non-limiting examples of solid fatty alcohols include cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, and a mixture thereof.

Many nonionic surfactants are known and useable in the hair-treatment compositions. Nonetheless, in some cases, the hair-treatment compositions may include one or more esters of polyols with fatty acids or alkoxylated derivatives thereof. Non-limiting examples include glyceryl distearate, glyceryl hydroxystearate, glyceryl laurate, glyceryl linoleate, glyceryl myristate, glyceryl oleate, glyceryl stearate, an ethoxylated derivate thereof, or a mixture thereof.

Non-silicone shine enhancers may include, for example, liquid fatty alcohols. Non-limiting examples of liquid fatty alcohols include 2-octyldodecanol, isostearyl alcohol, 2-hexyldecanol, 2-heptyldecanol, 2-octyldecanol, caproic alcohol (1-hexanol), enanthic alcohol (1-heptanol), caprylic alcohol (1-octanol), pelargonic alcohol (1-nonanol), capric alcohol (1-decanol), lauryl alcohol (1-dodecanol), and a mixture thereof Non-limiting examples of amidoamines include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and a mixture thereof.

Non-limiting examples of acids include glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, and a mixture thereof.

The hair-treatment compositions are useful in treating hair, for example, methods for conditioning hair or for providing conditioning benefits to hair. Non-limiting examples of conditioning benefits include imparting shine, color vibrancy, smoothness, softness, and discipline to the hair. The hair-treatment compositions may also be used to improve frizz control (i.e., to reduce frizz), provide end seal of split ends or reduce the development of split ends, and enhance root lift. The methods typically include applying a hair-treatment composition to the hair, allowing the hair treatment composition to remain on the hair for a period of time, and rinsing the hair-treatment composition from the hair. For example, the hair-treatment composition may be allowed to remain on the hair for about 5 second to about 30 minutes.

In some cases, the hair treatment compositions are applied to the hair shortly after the hair has been cleansed or shampooed, for example, while the hair is still wet or damp. After the hair-treatment composition has remained on the hair for a period of time, it is rinsed from the hair and the hair may optionally be further treated with, for example, a typical conditioning compositions (a conditioner) and/or styled. Alternatively, a hair-treatment composition may be applied to the hair before the hair is cleansed or shampooed. For example, the hair-treatment composition may be applied to the hair (wet or dry) and allowed to remain on the hair for a period of time and rinsed from the hair. After rinsing the hair-treatment composition from the hair, the hair is cleansed or shampooed and optionally treated with a typical conditioning composition (a conditioner).

In some instances, the hair-treatment compositions are particularly useful as an interim treatment, e.g., a treatment to the hair immediately after shampooing the hair but before conditioning the hair or immediately after chemically treating the hair but before cleansing or shampooing the hair. For example, after rinsing a chemical treatment composition from the hair, a hair-treatment composition according to the instant disclosure can be applied to the hair and allowed to remain on the hair for a period of time and rinsed from the hair. After rinsing the hair-treatment composition from the hair, the hair may be cleansed or shampooed, optionally treated with a conditioning composition (a conditioner), and styled. The hair-treatment composition is also particularly useful as an interim treatment between shampooing and conditioning. After a shampoo has been rinsed from the hair, for example, while the hair is still damp, a hair-treatment composition may be applied to the hair and allowed to remain on the hair for a period of time. After optionally rinsing the hair-treatment composition from the hair, the hair is conditioned (i.e., a conditioner is applied to the hair). After rinsing the conditioner from the hair, the hair may be styled, as desired.

The hair-treatment compositions may be included in a kit, for example, a kit comprising a hair-treatment composition, a shampoo, and optionally a conditioner. The hair-treatment composition, the shampoo, and the optional conditioner are separately contained or separately packaged. Kits according to the disclosure also include kits comprising a hair-treatment composition and one or more chemical hair-treatment compositions. Non-limiting examples of chemical hair-treatment compositions include hair lightening compositions, hair coloring compositions, hair relaxing compositions, hair straightening compositions, and hair shaping compositions (e.g., compositions to permanently curl hair).

BRIEF DESCRIPTION OF THE DRAWINGS

Implementations of the present technology will now be described, by way of example only, with reference to the attached figures, wherein.

Figure 1:
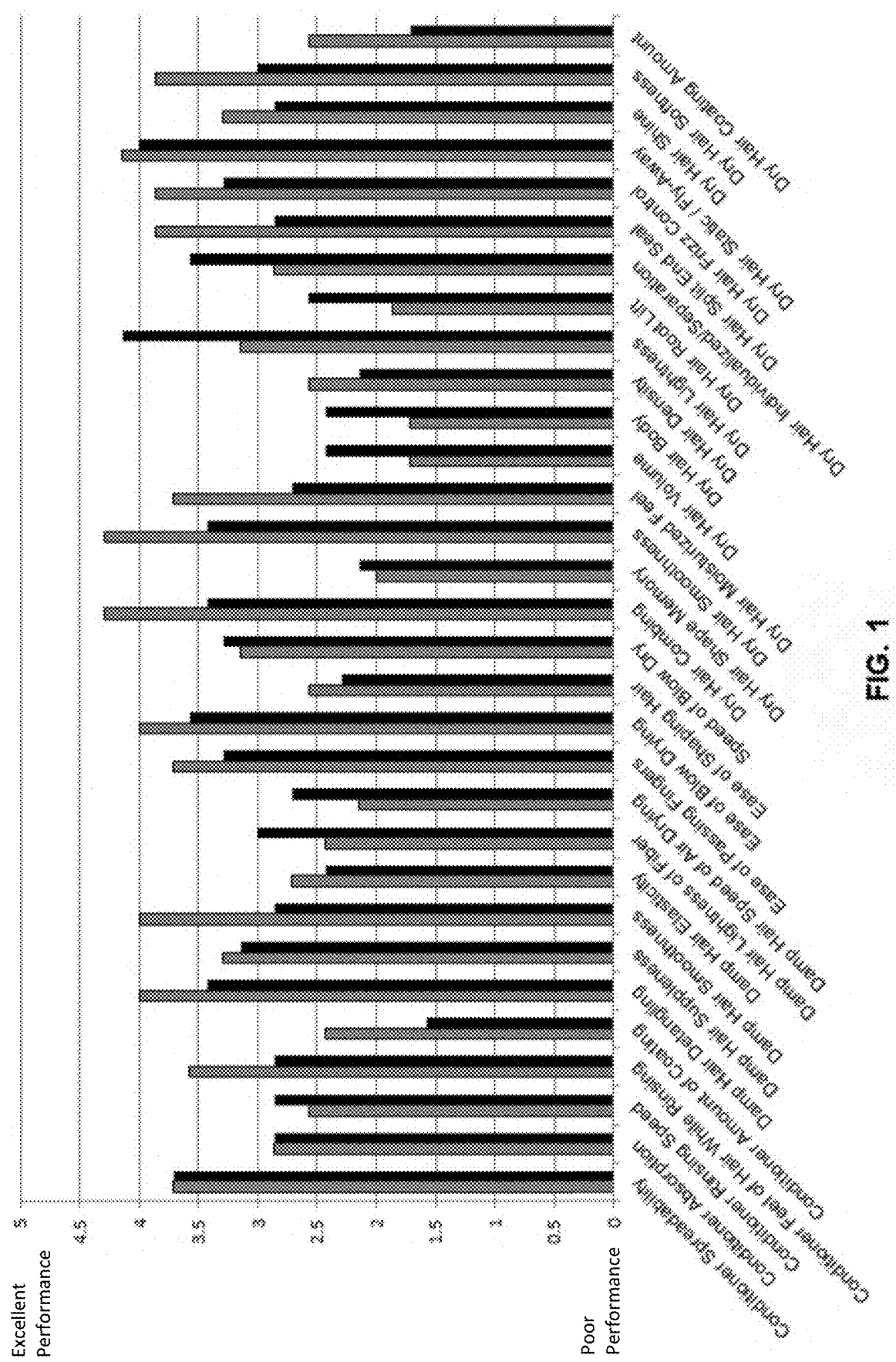
FIG. 1 is a bar graph comparing hair treated with a hair-treatment composition according to the instant disclosure (left bars, which are shaded), used as an interim treatment, with hair not treated with a hair-treatment composition according to the instant disclosure (right bars, which are solid)

It should be understood that the various aspects are not limited to the arrangements and instrumentality shown in the drawings.

DETAILED DESCRIPTION OF THE DISCLOSURE

The present disclosure relates to hair-treatment compositions, methods of using the hair-treatment compositions, and kits comprising the hair-treatment compositions. The term "hair-treatment composition" relates to a composition according to the present disclosure that is applied to the hair to improve the hair's cosmetic characteristics. Non-limiting, desirable properties that may be imparted to the hair include conditioning and style benefits such as imparting shine, color vibrancy, smoothness, softness, and discipline to the hair. Hair treated with the hair-treatment compositions becomes moisturized, soft, and silky; and is easy to detangle regardless of whether the hair is wet or dry.

The hair-treatment compositions of the disclosure typically include:
 (a) about 1 to about 3 wt. % of one or more vegetable oils;
 (b) about 2 to about 4 wt. % of one or more solid fatty alcohols;
 (c) one or more nonionic surfactants;
 (d) one or more non-silicone shine enhancers;
 (e) one or more amidoamines;
 (f) one or more acids; and
 (g) water.

The hair-treatment compositions typically have a fluid viscosity, for example a viscosity of less than 30 DU (Units of Deflection or "Deflection Units") at 25° C. In some instances, the viscosity may be about 10 to about 30 DU, about 10 to about 25 DU, about 10 to about 20 DU, about 15 to about 30 DU, or about 20 to about 30 DU. The viscosity may also be presented in the units "mPa·s." For instance, the hair-treatment compositions of the instant disclosure may have a viscosity of less than 250, less than 200, or less than 160 mPa·s at 25° C. Additionally, the viscosity may be about 40 to about 250 mPa·s, about 50 to about 250 mPa·s, about 75 to about 250 mPa·s, about 40 to about 200 mPa·s, about 50 to about 200 mPa·s, about 75 to about 200 mPa·s, about 40 to about 160 mPa·s, about 50 to about 160 mPa·s, about 75 to about 160 mPa·s, about 40 to about 125 mPa·s, or about 50 to about 125 mPa·s at 25° C.

The viscosity can be measured using a Rheomat 180, 108E, ER10, 200 or TVe-05 viscometer from proRheo or PCE Instruments or Lamy Technology. The viscosity measurement is generally performed from 20 to 25 degrees centigrade, wherein the Rheomat viscometer is equipped with a particular-sized spindle (e.g., #2, 3, or 4), the measurement being performed after a few minutes (e.g., 10 minutes) of rotation of the spindle in a composition (after which time stabilization of the viscosity and of the spin speed of the spindle are observed), at a specified shear rate (e.g., 200 s-1).

The hair-treatment compositions typically have a low pH of less than 7. In some cases, the pH of the hair-treatment compositions may be about 2 to about 6, about 3 to about 6, about 3 to about 5, or about 3 to about 4.

The hair-treatment compositions do not require synthetic compounds including synthetic silicone compounds. Thus, the hair-treatment compositions may be free or essentially free of silicones and/or free or essentially free of other synthetic components. Thus, in some instances, the hair-treatment compositions according to the disclosure may be "natural hair-treatment compositions." The term "natural" may be used in the present disclosure to specify that the composition is free or essentially free of synthetic ingredients. The term "natural" may also be used in the present disclosure to specify that the composition contains natural-based ingredients such as plant- or vegetable-derived ingredients, for example, the vegetable oils of the disclosure.

As noted previously, the hair-treatment compositions of the instant disclosure provide styling and conditioning benefits to the hair. Many typical products that provide conditioning benefits to hair include cationic surfactants selected from quaternary ammonium compounds (e.g., behentrimonium chloride, cetrimonium chloride, behentrimonium methosulfate) and/or quaternary ammonium polymers (e.g., polyquaterniums). The hair-treatment compositions of the instant disclosure, however, employ one or more amidoamine compounds which help provide conditioning benefits; amidoamine compounds can function as a cationic conditioning compound depending on the final pH of the hair-treatment compositions of the instant disclosure. Thus, cationic compounds selected from quaternary ammonium compounds (e.g., behentrimonium chloride, cetrimonium chloride, behentrimonium methosulfate) and/or quaternary ammonium polymers (e.g., polyquaterniums) are not required in the hair-treatment compositions and therefore the hair-treatment compositions of the instant disclosure may be free or essentially free of cationic compounds selected from quaternary ammonium compounds (e.g., behentrimonium chloride, cetrimonium chloride, behentrimonium methosulfate) and/or quaternary ammonium polymers (e.g., polyquaterniums).

A vegetable oil is an oil derived from a plant, for example, oils from seeds or fruits. Non-limiting examples of vegetable oils include coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof. In some cases, the hair-treatment composition includes at least coconut oil. Also useful is a combination of coconut oil and soybean oil.

In an embodiment, the vegetable oils in the composition of the present disclosure are chosen from coconut oil and soybean oil, or a mixture thereof.

In an embodiment, the vegetable oils in the composition of the present disclosure comprise coconut oil.

In an embodiment, the vegetable oils in the composition of the present disclosure comprise soybean oil.

Typically, the hair-treatment compositions include about 1 to about 3 wt. % of one or more vegetable oils, based on the total weight of the hair-treatment composition. The total amount of the one or more vegetable oils may be about 1 to about 2.5 wt. %, about 1.5 to about 3 wt. %, or about 1.5 to about 2.5 wt. %, based on the total weight of the hair-treatment composition.

The solid fatty alcohol(s) may be crystalline, amorphous or pasty. The solid fatty alcohol(s) are solid at room temperature (25 degrees centigrade) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight.

In some cases, the solid fatty alcohols may have a melting point of greater than or equal to 28° C. and have a viscosity, at a temperature of 40° C. and at a shear rate of 1 s"1, of greater than or equal to 1 Pa·s. Furthermore, in some cases, the melting point of the fatty alcohols ranges from 30° C. to 250° C., such as from 32° C. to 150° C. or such as from 35° C. to 150° C.

The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 8 to 40 carbon atoms, such as from 10 to 30 carbon atoms, or such as from 12 to 24 carbon atoms. The solid fatty alcohols preferably have the structure of formula: R—OH in which R especially denotes a C6-C60, for example, C8-C60, preferably C10-C50 or even C12-C30 alkyl group, R possibly being substituted with one or more hydroxyl groups, R possibly being branched.

Non-limiting examples of solid fatty alcohols include myristyl alcohol, cetyl alcohol, stearyl alcohol, behenyl alcohol, and mixtures thereof. Other suitable non-limiting examples of solid fatty alcohols include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

The solid fatty alcohol may represent a mixture of fatty alcohols, which means that several species of fatty alcohol may coexist, in the form of a mixture, in a commercial product. The solid fatty alcohols of the invention are preferably non-oxyalkylenated and/or non-glycerolated. These fatty alcohols may be constituents of animal or plant waxes.

In some instances, the solid fatty alcohols are chosen from cetyl alcohol, stearyl alcohol and mixtures thereof (cetyl-stearyl alcohol or cetearyl alcohol).

The total amount of the solid fatty alcohols is typically about 2 to about 4 wt. %, based on the total weight of the hair-treatment composition. The total amount of the one or more solid fatty alcohol may be about 2 to about 3.5 wt. %, about 2.5 to about 4 wt. %, or about 2.5 to about 3.5 wt. %, based on the total weight of the hair-treatment composition.

Many nonionic surfactants are known and may be useful in the hair-treatment compositions of the instant disclosure. Non-limiting classes of nonionic surfactants include esters of polyols with fatty acids and alkoxylated derivatives thereof, alkylpolyglucosides, sucrose esters, alkoxylated ethers of fatty acids and glucose or alkylglucose, esters of fatty acids and glucose or alkylglucose, sorbitol esters of fatty acids and alkoxylated derivatives thereof, alkoxylated fatty alcohols (for example, ethoxylated fatty alcohols), alkanolamides, and a mixture thereof. A more exhaustive list of anionic surfactants that may be included in the hair-treatment compositions is provided later, under the heading "Nonionic Surfactants."

In some instances, the hair-treatment compositions include one or more esters of polyols with fatty acids or alkoxylated derivatives thereof as at least one of the one or more nonionic surfactants. Non-limiting examples include glyceryl distearate, glyceryl hydroxystearate, glyceryl laurate, glyceryl linoleate, glyceryl myristate, glyceryl oleate, glyceryl stearate, an ethoxylated derivate thereof, and a mixture thereof. In some cases, glyceryl stearate is particularly useful.

In an embodiment, the nonionic surfactants in the composition of the present disclosure are chosen from glyceryl oleate, glyceryl stearate, or a mixture thereof.

In an embodiment, the nonionic surfactants in the composition of the present disclosure comprise glyceryl oleate.

In an embodiment, the nonionic surfactants in the composition of the present disclosure comprise glyceryl stearate.

The total amount of the one or more nonionic surfactants can range from about 0.05 to about 15 wt. %, based on the total weight of the hair-treatment composition. The total amount of the one or more nonionic surfactants may be from about 0.05 to about 10 wt. %, about 0.1 to about 5 wt. %, or about 0.1 to about 4 wt. %, or about 0.15 to about 3 wt. %, or about 0.15 to about 2.5 wt. %, or about 0.15 to about 2 wt. %, or about 0.15 to about 1.5 wt. %, based on the total weight of the hair-treatment composition Non-silicone shine enhancers are compounds that impart, improve, or enhance shine to hair. The compounds themselves may be responsible for the shine or may interact with other compounds in the hair-treatment composition to improve or enhance the shine of hair.

In some cases, one or more of the shine enhancers is a liquid fatty alcohol such as those chosen from saturated or unsaturated, linear or branched alcohols comprising from 6 to 50 carbon atoms and preferably from 8 to 30 carbon atoms. The liquid fatty alcohol(s) are liquid at room temperature (25 degrees centigrade) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, or liquid petroleum jelly or other cosmetically acceptable organic solvent) to at least 1% by weight. Mention may be made, for example, of octyldodecanol, 2-butyloctanol, 2-hexyldecanol, 2-undecylpentadecanol, oleyl alcohol or linoleyl alcohol. The saturated liquid fatty alcohols can be branched. They can optionally comprise, in their structure, at least one aromatic or non-aromatic ring. They can be acyclic. Among liquid saturated fatty alcohols, octyldodecanol, isostearyl alcohol and 2-hexyldecanol can be cited.

The unsaturated liquid fatty alcohols may exhibit, in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

The total amount of the one or more non-silicone shine enhancers may vary but is typically about 0.01 to about 10 wt. %, based on the total weight of the hair-treatment composition. In some instances, the total amount of the one or more non-silicone shine enhancers is about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, or about 0.1 to about 3 wt. %, based on the total weight of the hair-treatment composition.

Amidoamines are a class of chemical compounds that are formed from fatty acids and diamines. Non-limiting examples of amidoamines include those of the following formula:

RCONHR'N(R")$_2$ wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Non-limiting examples of amidoamines include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palmitamidopropyl dimethylamine, stearamidoethyldiethylamine, and a mixture thereof. In some cases, brassicamidopropyl dimethylamine may be particularly useful.

In an embodiment, the amidoamine in the composition of the present disclosure comprises brassicamidopropyl dimethylamine.

In an embodiment, the amidoamine in the composition of the present disclosure comprises stearamidopropyl dimethylamine.

The total amount of the one or more amidoamines in the hair-treatment compositions can vary but is typically about 0.1 to about 15 wt. %, based on the total weight of the hair-treatment composition. In some instances, the total amount of the one or more amidoamines may be about 0.1 to about 12 wt. %, about 0.1 to about 10 wt. %, about 0.1 to about 8 wt. %, about 0.1 to about 6 wt. %, about 0.1 to about 5 wt. %, about 1 to about 15 wt. %, about 1 to about 12 wt. %, about 1 to about 10 wt. %, about 1 to about 8 wt. %, about 1 to about 6 wt. %, or about 1 to about 5 wt. %, based on the total weight of the hair-treatment composition.

The hair-treatment compositions typically include one or more acids. The acids may be used, for example, to neutralize the one or more amidoamines and/or to achieve a desired pH. Non-limiting examples of useful acids include glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, and a mixture thereof.

The acids are typically non-polymeric and may have one (mono), two (di), or three (tri) carboxylic acid groups (—COOH). The non-polymeric mono, di, and tricarboxylic adds, and/or salts thereof, typically have a molecular weight of less than about 500 g/mol, less than about 400 g/mol, or less than about 300 g/mol.

Non-limiting examples of monocarboxylic acids include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof.

Non-limiting examples of dicarboxylic acids include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof.

Non-limiting examples of tricarboxylic acids include citric acid, isocitric acid, aconitric acid, propane-1,2,3-tricarboxylic acid, benzene-1,3,5-tricarboxylic acid, a salt thereof, and a mixture thereof.

The total amount of the one or more acids may vary but is typically about 0.01 to about 5 wt. %, based on the total weight of the hair-treatment composition. In some cases, the total amount of the one or more acids is about 0.01 to about 4 wt. %, about 0.01 to about 3 wt. %, about 0.01 to about 2 wt. %, about 0.05 to about 5 wt. %, about 0.05 to about 4 wt. %, about 0.05 to about 3 wt. %, about 0.05 to about 2 wt. %, about 0.1 to about 5 wt. %, about 0.1 to about 4 wt. %, about 0.1 to about 3 wt. %, about 0.1 to about 2 wt. % or about 0.1 to about 1 wt. %, based on the total weight of the hair-treatment composition.

In one embodiment, the hair-treatment composition may include:
  (a) about 1 to about 3 wt. % of one or more vegetable oils, for example coconut oil, soybean oil, or a mixture thereof;
  (b) about 2 to about 4 wt. % of one or more straight chain fatty alcohols, for example cetearyl alcohol;
  (c) 1 wt. % or less of one or more esters of polyols with fatty acids or alkoxylated derivatives thereof, for example, glyceryl distearate, glyceryl hydroxystearate, glyceryl laurate, glyceryl linoleate, glyceryl myristate, glyceryl oleate, glyceryl stearate, an ethoxylated derivate thereof, or a mixture thereof;
  (d) about 0.1 to about 5 wt. % of one or more non-silicone shine enhancers, wherein the non-silicone shine enhancer is a branched chain fatty alcohol, for example, 2-octyldodecanol;

(e) about 1 to about 15 wt. %, about 1 to about 10 wt. %, or about 1 to about 5 wt. % of one or more amidoamines of the formula:

wherein R is a linear or branched, acyclic alkyl or alkenyl group or an alkyl phenyl group; R' is a divalent hydrocarbon radical containing less than 6 carbon atoms; and R" is H or a hydrocarbon radical containing less than 6 carbon atoms, for example, brassicamidopropyl dimethylamine;

(f) about 0.01 to about 5 wt. %, about 0.1 to about 5 wt. %, or about 0.1 to about 2 wt. % of one or more non-polymeric mono-, di-, or tricarboxylic acids; and (g) about 60 to about 95 wt. %, about 70 to about 95 wt. %, or about 80 to about 95 wt. % of water.

The hair-treatment composition has a fluid viscosity, for example a viscosity of less than 30 DU at 25° C., using a spindle #2. Additionally, the hair-treatment composition has a pH of less than 7. In some cases, the pH of the hair-treatment composition may be about 2 to about 6, about 3 to about 6, or about 3 to about 5 or about 3 to about 4.

The hair-treatment composition does not require synthetic compounds including synthetic silicone compounds. Thus, the hair-treatment composition may be free or essentially free of silicones and/or free or essentially free of other synthetic components. Accordingly, the hair-treatment composition may be a natural hair-treatment composition. Moreover, the hair-treatment composition may be free or essentially free of cationic compounds selected from quaternary ammonium compounds (e.g., behentrimonium chloride, cetrimonium chloride, behentrimonium methosulfate) and quaternary ammonium polymers (e.g., polyquaterniums). Finally, the hair-treatment compositions may be free or essentially free of alkoxylated (including ethoxylated) compounds.

The hair-treatment compositions are useful in treating hair, for example, methods for conditioning hair or for providing conditioning benefits to hair. Non-limiting examples of conditioning benefits include imparting shine, color vibrancy, smoothness, softness, and discipline to the hair. The hair-treatment compositions may also be used to improve frizz control (i.e., to reduce frizz), provide end seal of split ends or reduce the development of split ends, and enhance root lift. The methods typically include applying a hair-treatment composition to the hair, allowing the hair treatment composition to remain on the hair for a period of time, and rinsing the hair-treatment composition from the hair.

For example, the hair-treatment composition may be allowed to remain on the hair for about 5 second to about 30 minutes. The hair-treatment composition may be allowed to remain on the hair for about 5 seconds to about 25 minutes, about 5 seconds to about 20 minutes about 5 seconds to about 15 minutes, about 5 seconds to about 10 minutes, about 30 seconds to about 30 minutes, about 30 seconds to about 25 minutes, about 30 seconds to about 20 minutes, about 30 seconds to about 15 minutes, about 30 seconds to about 10 minutes, about 1 minute to about 30 minutes, about 1 minute to about 25 minutes, about 1 minute to about 20 minutes, about 1 minute to about 15 minutes, about 1 minute to about 10 minutes. In particular, the hair-treatment composition may be allowed to remain on the hair for about 2 minutes to about 15 minutes, or about 3 minutes to about 12 minutes, or about 5 minutes to about 10 minutes.

In some cases, the hair treatment compositions are applied to the hair shortly after the hair has been cleansed or shampooed, for example, while the hair is still wet or damp. After the hair-treatment composition has remained on the hair for a period of time (e.g., about 5 minutes), it is rinsed from the hair and the hair may optionally be further treated with, for example, a typical conditioning composition (a conditioner) and/or styled. Alternatively, a hair-treatment composition may be applied to the hair before the hair is cleansed or shampooed or chemically treated. For example, the hair-treatment composition of the instant disclosure may be applied to the hair (wet or dry) as a pre-treatment composition and allowed to remain on the hair for a period of time (e.g., about 5 to 10 minutes) and rinsed from the hair. After rinsing the hair-treatment from the hair, the hair is cleansed or shampooed and optionally treated with a typical conditioning composition (a conditioner).

In some instances, the hair-treatment compositions are particularly useful as an interim treatment, e.g., a treatment to the hair immediately after shampooing the hair but before conditioning the hair or immediately after chemically treating the hair but before cleansing or shampooing the hair. For example, after rinsing a chemical treatment composition from the hair, a hair-treatment composition according to the instant disclosure can be applied to the hair and allowed to remain on the hair for a period of time (e.g., about 5 to about 10 minutes) and rinsed from the hair. After rinsing the hair-treatment composition from the hair, the hair may be cleansed or shampooed, optionally treated with a conditioning composition (a conditioner), and styled. The hair-treatment composition is also particularly useful as an interim treatment between shampooing and conditioning. After a shampoo has been rinsed from the hair, for example, while the hair is still damp, a hair-treatment composition may be applied to the hair and allowed to remain on the hair for a period of time. After optionally rinsing the hair-treatment composition from the hair, the hair is conditioned (i.e., a conditioner is applied to the hair). After rinsing the conditioner from the hair, the hair may be styled, as desired.

The hair-treatment compositions may be "layered" onto other hair-treatment compositions that have already been applied to the hair. The term "layered" means that the hair-treatment rinse is applied to the hair on which another composition has already been applied. For example, a shampoo, a conditioner, or a chemical hair treatment may first be applied to the hair. Without first rinsing the shampoo, the conditioner, or the chemical hair treatment from the hair, a hair-treatment composition according to the instant disclosure may be layered on top of the shampoo, conditioner, or chemical hair treatment (which is already on the hair), and the hair-treatment composition allowed to remain on the hair for a period of time before rinsing it, along with the underlying composition, from the hair.

In some instances, the hair-treatment compositions are particularly useful either as a rinse-off or a leave-on post-treatment, e.g., a treatment to the hair immediately after treating the hair with a rinse-off conditioner or immediately after chemically treating the hair. For example, after rinsing a chemical treatment composition from the hair, a hair-treatment composition according to the instant disclosure can be applied to the hair and allowed to remain on the hair for a period of time (e.g., about 5 to about 10 minutes) and rinsed from the hair. After rinsing the hair-treatment composition from the hair, the hair may be cleansed or shampooed, optionally treated with a conditioning composition (a conditioner), and styled. In another example, after rinsing a conditioner from the hair, a hair-treatment composition according to the instant disclosure can be applied to the wet, damp or dry hair as a leave-on composition and the hair may then be styled, as desired. In some cases, when used as a post-treatment composition, the hair-treatment composition according to the instant disclosure can be used to protect the hair from damage from heat (for example, heat produced with the use of a blow dryer or flat iron or heating lamp or hood dryer on hair).

The hair-treatment compositions may be included in a kit, for example, a kit comprising a hair-treatment rinse, a shampoo, and optionally a conditioner. The hair-treatment composition (rinse-off or leave-on), the shampoo, and the optional conditioner are separately contained or separately packaged. Kits according to the disclosure also include kits comprising a hair-treatment composition and one or more chemical hair-treatment compositions. Non-limiting examples of chemical hair-treatment compositions include hair lightening compositions, hair coloring compositions, hair relaxing compositions, hair straightening compositions, and hair shaping compositions (e.g., compositions to permanently curl hair).

More exhaustive but non-limiting lists of components that are useful in the hair-treatment compositions of the instant disclosure are presented below.

Solid Fatty Alcohol

The solid fatty alcohol may be crystalline, amorphous or pasty. The solid fatty alcohols are solid at room temperature (25 degrees centigrade) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight.

In some cases, the solid fatty alcohols preferably have a melting point of greater than or equal to 28° C. and have a viscosity, at a temperature of 40° C. and at a shear rate of 1 s"1, of greater than or equal to 1 Pa·s. Moreover, the melting point of the fatty alcohols may ranges from 30° C. to 250° C., such as from 32° C. to 150° C. or such as from 35° C. to 150° C. The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 8 to 40 carbon atoms, such as from 10 to 30 carbon atoms, or such as from 12 to 24 carbon atoms.

The solid fatty alcohols preferably have the structure of formula: R—OH in which R especially denotes a C6-C60, for example, C8-C60, preferably C10-C50 or even C12-C30 alkyl group, R possibly being substituted with one or more hydroxyl groups, R possibly being branched.

In an embodiment, the solid fatty alcohols are chosen from myristyl alcohol, cetyl alcohol, stearyl alcohol and behenyl alcohol, and mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

The solid fatty alcohol may represent a mixture of fatty alcohols, which means that several species of fatty alcohol may coexist, in the form of a mixture, in a commercial product.

The solid fatty alcohols of the invention are preferably non-oxyalkylenated and/or non-glycerolated. These fatty alcohols may be constituents of animal or plant waxes.

In an embodiment, the solid fatty alcohols are chosen from cetyl alcohol, stearyl alcohol and mixtures thereof (cetylstearyl alcohol or cetearyl alcohol).

Non-Silicone Shine Enhancers

The hair-treatment compositions include one or more non-silicone shine enhancers, including at least one liquid fatty alcohol chosen from saturated or unsaturated, linear or branched alcohols comprising from 6 to 50 carbon atoms and preferably from 8 to 30 carbon atoms. The liquid fatty alcohol(s) are liquid at room temperature (25 degrees centigrade) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight. Mention may be made, for example, of octyldodecanol, 2-butyloctanol, 2-hexyldecanol, 2-undecylpentadecanol, oleyl alcohol or linoleyl alcohol.

The saturated liquid fatty alcohols can be branched. They can optionally comprise, in their structure, at least one aromatic or non-aromatic ring. They can be acyclic. Among liquid saturated fatty alcohols, octyldodecanol, isostearyl alcohol and 2-hexyldecanol can be cited.

The unsaturated liquid fatty alcohols may exhibit in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The surfactants preferably contain a number of moles of ethylene oxide and/or of propylene oxide of between 2 and 100 and most preferably between 2 and 50.

In accordance with one preferred embodiment of the invention, the oxyalkylenated nonionic surfactants are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic surfactants, polyglycerolated $C_8$-$C_{40}$ alcohols are preferably used.

In particular, the polyglycerolated $C_8$-$C_{40}$ alcohols correspond to the following formula:

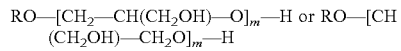

RO—[$CH_2$—CH($CH_2$OH)—O]$_m$—H or RO—[CH($CH_2$OH)—$CH_2$O]$_m$—H in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucoside and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

It is preferable that the nonionic surfactant be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

Preferably, the nonionic surfactant may be a nonionic surfactant with an HLB of 18.0 or less, such as from 4.0 to 18.0, more preferably from 6.0 to 15.0 and furthermore preferably from 9.0 to 13.0. The HLB is the ratio between the hydrophilic part and the lipophilic part in the molecule.

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Amidoamines

In some cases, useful amidoamine compounds are those corresponding to the following formula and their salts:

RCONHR'N(R")$_2$ wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palmitamidopropyl dimethylamine, stearamidoethyldiethylamine, and mixtures thereof.

Acids

The at least one acid may be chosen from organic acids such as mono-carboxylic acids and polycarboxylic acids (with 2 or more carboxylic acid groups).

Suitable examples of the organic acid include acetic acid, terephthalic acid, HOOC-PEG-COOH acid; citric acid, tartaric acid; betaine hydrochloride, gluconic acid or 2-ethylcaproic acid, lactic acid, salicylic acid, glycolic acid, malic acid, maleic acid, oxalic acid, malonic acid, aspartic acid, glutamic acid, benzoic acid, acetic acid, formic acid, and mixtures thereof Other suitable examples of the at least organic acid are chosen from polycarboxylic acids selected from aspartic acid, glutamic acid, oxalic acid, succinic acid, tartaric acid, mucic acid, citric acid, malic acid, maleic acid, phthalic acid, poly(ethylene glycol) bis(carboxymethyl)ethers, acrylic polyacid, copolymer of acrylic acid and maleic acid, polyaspartic acid, and carboxylic polydimethylsiloxanes.

In other embodiments, the organic acid is a sulfonic acid selected from benzene sulfonic acid, sulfonic acid HSO2OH, taurine, 2-[4-(2-hydroxy-ethyl)-piperazin-1-yl] ethane sulfonic acid (or HEPES), and (3E)-3-(4-{(E)-[7,7-dimethyl-3-oxo-4-(sulfomethyl)bicyclo[2.2.1]hept-2-ylidene]methyl}benzylidene)-7,7-dimethyl-2-oxobicyclo [2.2.1]hept-1-yl]methane sulfonic acid. In an embodiment, the organic acid is selected from trichloroacetic acid, L-glutamic acid, lactic acid, succinic acid, tartaric acid, poly (ethylene glycol) bis(carboxymethyl)ether having a molecular weight of 250 g/mol, salicylic acid derivatives, jasmonic acid derivative, 3-hydroxy-2-pentyl-cyclopentyl acetic acid, 2-[4-(2-hydroxy-ethyl)-piperazin-1-yl]-ethanesulfonic acid, malic acid, pyruvic acid, and mandelic acid.

In an embodiment, the organic acid is selected from tartaric acid, lactic acid, malic acid, maleic acid, oxalic acid, malonic acid, citric acid, aspartic acid, glutamic acid, salicylic acid, benzoic acid, acetic acid, formic acid and mixtures thereof.

Cosmetically Acceptable Carrier

In addition to water, the cosmetically acceptable carrier can include, for example, glycerin, 01-4 alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Thickening Agents

The hair-treatment compositions may contain one or more thickeners or viscosity modifying agents. Classes of such agents include, but are not limited to, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof. Natural thickening agent agents are preferred.

The total amount of the one or more thickening agents may vary, but in some cases is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about wt. %, about 0.5 to about 5 wt. %, about 1 to about 10 wt. %, about 1 to about 8 wt. %, about 1 to about 6 wt. %, or about 1 to about 5 wt. %, based on the total weight of the composition.

Preservatives

One or more preservatives may be included in the hair-treatment compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair care formulations depending on the specific combination of other components, the form of the compositions, and/or the use of the formulation. In various embodiments, the hair treatment compostions according to the instant disclosure can be in the form of a hair spray, lotion (e.g., a milky lotion), light serum, light cream, conditioner, or non-aerosolized hair spray (for example, packaged as a pump spray or squeeze-bottle spray).

Implementation of the present disclosure is provided by way of the following examples. The examples serve to illustrate the technology without being limiting in nature.

Example 1

Formulations

| | INCI US | Comparative | | | | | | | Inventive | | |
|---|---|---|---|---|---|---|---|---|---|---|---|
| | | 1 | 2 | 3 | 4 | 5 | 6 | 7 | 8 | 9 | 10 |
| Vegetable Oil | COCONUT OIL | 2 | 2 | 2 | 2 | 2 | 2 | | 1 | 1.5 | |
| | SOYBEAN OIL | 0.01 | 0.01 | 0.01 | 0.01 | 0.01 | 0.01 | 2.01 | 0.01 | 0.01 | 1.01 |
| Solid Fatty Alcohol | CETEARYL ALCOHOL | 3 | 3 | 4 | 2 | 3 | 3 | 3 | 3 | 3 | 3 |
| Nonionic Surfactants | GLYCERYL STEARATE | 0.15 | | 0.15 | 0.15 | 0.15 | 0.15 | 0.15 | 0.15 | 0.15 | 0.15 |
| | GLYCERYL OLEATE | | | | | | 1 | | | | |
| Non-Silicone Shine Enhancer | OCTYLDODECANOL | | | | | | | | 0.5 | 0.5 | 0.5 |
| Amidoamine | BRASSICAMIDOPROPYL DIMETHYLAMINE | 2.5 | 2.5 | 2.5 | 2.5 | 2.5 | 2.5 | 2.5 | 2.5 | 2.5 | 2.5 |

-continued

|  | INCI US | Comparative | | | | | | | Inventive | | |
|---|---|---|---|---|---|---|---|---|---|---|---|
|  |  | 1 | 2 | 3 | 4 | 5 | 6 | 7 | 8 | 9 | 10 |
| Acid | TARTARIC ACID | 0.4 | 0.4 | 0.4 | 0.4 | 0.5 | 0.4 | 0.5 | 0.4 | 0.5 | 0.5 |
| Solvent | CAPRYLYL GLYCOL AND/OR GLYCERIN | 0.3 | 0.3 | 0.3 | 0.4 | 0.3 | 0.3 | 0.3 | 0.3 | 0.3 | 0.3 |
| Additives | PRESERVATIVES AND/OR FRANGRANCE | <2 | <2 | <2 | <2 | <2 | <2 | <2 | <2 | <2 | <2 |
| Water | WATER | QS 100 | QS 100 | QS 100 | QS 100 | QS 100 | QS 100 | QS 100 | QS 100 | QS 100 | QS 100 |

The formulations in the table above may be made by first heating water to about 70° C. While stirring the water, brassicamidopropyl dimethylamine is added to the water. After the brassicamidopropyl dimethylamine is mixed in the water, tartaric acid is added to neutralize the brassicamidopropyl dimethylamine. After neutralization, the remaining ingredients may be added and mixed.

The viscosity of the inventive formulations was found to be less than 30 DU (Units of Deflection or "Deflection Units") at 25° C., 200 RPM, 30 sec using a spindle #2 (Rheomat 180). In some instances, the viscosity may be about 10 to about 30 DU, about 10 to about 25 DU, about 10 to about 20 DU, about 15 to about 30 DU, or about 20 to about 30 DU. The inventive formulations had a fluid viscosity and a milky appearance (similar to the viscosity ranging from that of evaporated milk which may be characterized as having a viscosity of 80 mPa·s at 40° C. to that of yogurt which may be characterized as having a viscosity of 150 mPa·s at 40° C.).

Example 2

Post-Shampoo Comparison

The inventive composition of Formulation #9 of Example 1 was evaluated against Comparative Formulation #1 of Example 1. The hair of volunteers was shampooed. After rinsing the shampoo from the hair, Inventive Formulation #9 was applied to half of the damp hair (applied to half of the head). Comparative Formulation #1 was applied to the other half of the hair (the other half of the head). Both Inventive Formulation #9 and Comparative Formulation #1 were allowed to remain on the hair for about 5 minutes. After rinsing both Inventive Formulation #9 and comparative Formulation #1 from the hair, the hair was combed, dried, and styled. The hair was evaluated by stylists throughout the entire process, and the results are summarized in the table below.

| Treatment Stage | Left Side of Head Inventive Formulation #9 | Right Side of Head Comparative Formulation #1 |
|---|---|---|
| Application | Formulation #9 absorbs into the hair causing a noticeable transformation in the texture of the hair | Formulation #1 does not absorb into the hair as much as Formulation #9; it retains more topical properties without transforming the texture of the hair |
| Rinsing | Hair treated with Formulation #9 had a more "slimy" feel, was more compact, and smooth | Hair treated with Formulation #1 had more mass (was not as compact) and was not as "slimy" and smooth as the hair treated with Formulation #9 |
| Wet hair | Hair treated with Formulation #9 was easy to comb and smooth | Hair treated with Formulation #1 exhibited slight tugging when combed but exhibited a clean and textured feel; the hair was also supple and exhibited root lift |
| Dry Hair | Hair treated with Formulation #9 exhibited improved: styleability; shape; style memory; discipline/control; end seal; even smoothness; and shine | Hair treated with Formulation #1 exhibited: slight frizz; and thicker/fuller look & feel |
| Stylist Preference | All stylist preferred Formulation #9 over Formulation #1 | No stylist preferred Formulation #1 over Formulation #9 |

Example 3

Interim Treatment Evaluation

Testing was carried out to determine the influence of Inventive Formulation #8 of Example 1 used as an interim treatment between shampooing and conditioning the hair. The entire head of hair of volunteers was first washed with a commercially available shampoo. After rinsing the shampoo from the hair, while the hair was still damp, half of the hair (half of the head of hair) was treated with Inventive Formulation #8. Inventive Formulation #8 was applied and allowed to remain on the hair for about 5 minutes before being rinsed from the hair. After Inventive Formulation #8 was rinsed from the hair, the entire head of hair was conditioned with a commercially available conditioner. Both halves of the head of hair (the half treated with Inventive Formulation #8 and the half not treated with Inventive Formulation #8) were evaluated across a large number of cosmetic attributes. Each attribute was ranked on a scale from 0 to 5, where "0" represents "poor performance" and "5" represents "excellent performance." The results are presented in the graph provided in FIG. 1. The shaded bar on the left represents Inventive Formulation #8; and the solid bar on the right represents the hair not treated with Inventive Formulation #8. The data show that hair treated with Inventive Formulation #8 was more compact with overall less volume (less frizz). The hair was smoother, softer, and appeared healthier than the hair not treated with Inventive Formulation #8. Also, the hair treated with Inventive Formulation #8 exhibited improved end seal, frizz control, was moisturized, was easier to detangle or comb regardless of whether the hair was wet or dry, and was shinier when dry.

Example 4

Comparative Interim Treatment Evaluation

Figure 2:
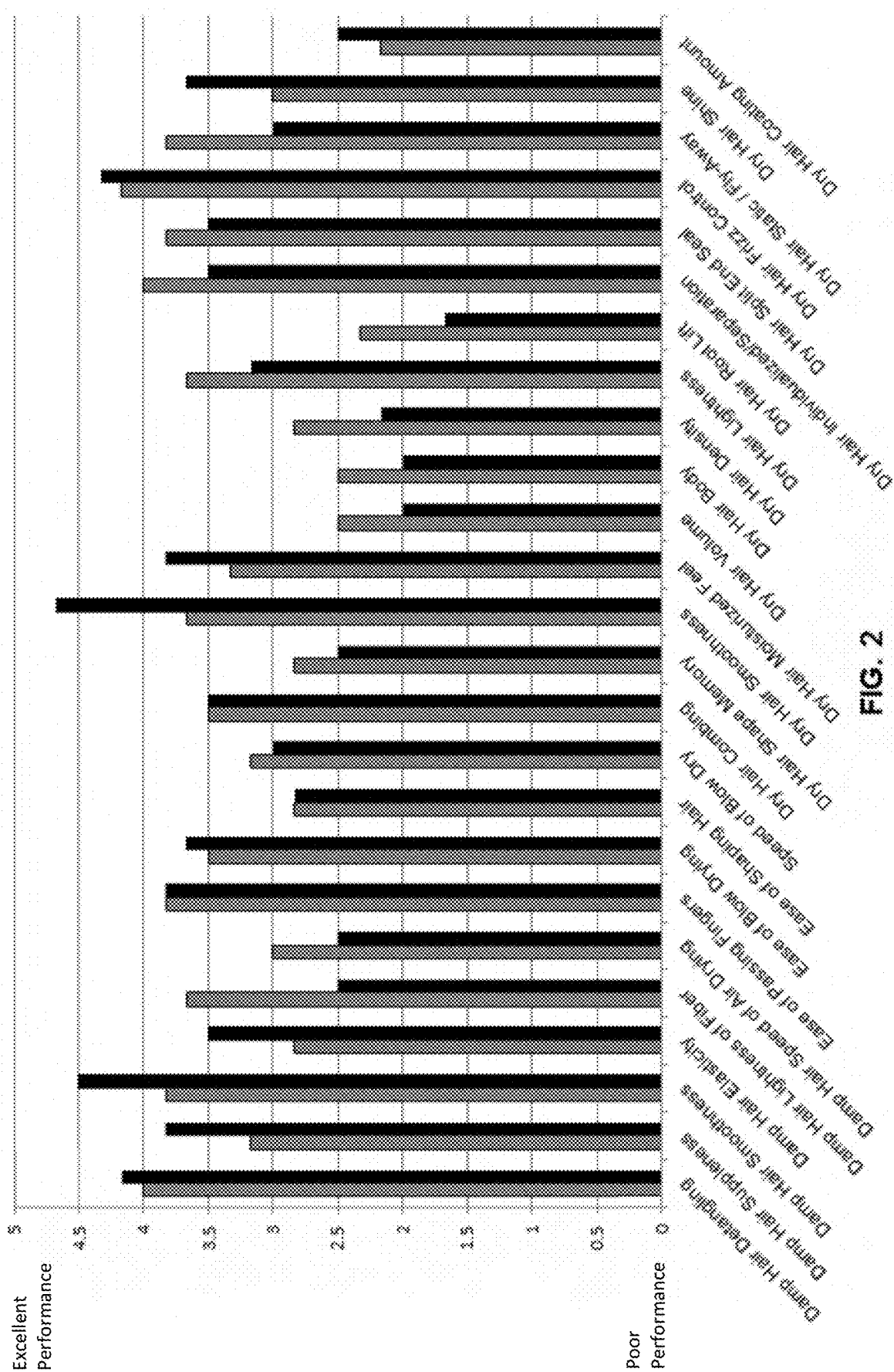
FIG. 2 is a bar graph comparing hair treated with a hair-treatment composition according to the instant disclosure (right bars, which are solid), used as an interim treatment, with hair treated with a comparative hair-treatment composition (left bars, which are shaded), also used as an interim treatment.

Testing was carried out to determine the influence of Inventive Formulation #8 of Example 1 against Comparative Formulation #5 of Example 1, used as an interim treatment between shampooing and conditioning the hair. The entire head of hair of volunteers was first washed with a commercially available shampoo. After rinsing the shampoo from the hair, while the hair was still damp, half of the hair (half of the head of hair) was treated with Inventive Formulation #8 and the other half of the hair (the other half of the head of hair) was treated with Comparative Formulation #5. Both formulations were applied and allowed to remain on the hair for about 5 minutes before being rinsed from the hair. After Inventive Formulation #8 and comparative Formulation #5 were rinsed from the hair, the entire head of hair was conditioned with a commercially available conditioner. Both halves of the head of hair were evaluated across a large number of cosmetic attributes. Each attribute was ranked on a scale from 0 to 5, where "0" represents "poor performance" and "5" represents "excellent performance." The results are presented in the graph provided in FIG. 2. The data show that hair treated with Inventive Formulation #8 was smoother, shinier, and overall more compact with reduced volume (less frizz) compared to hair treated with Comparative Formulation #5. Additionally, damp hair was more supple, smooth, and elastic, as shown in FIG. 2. The solid bar on the right represents Inventive Formulation #8; and the shaded bar on the left represents Comparative Formulation #5.

Example 5

Post Treatment Evaluation

Figure 3:
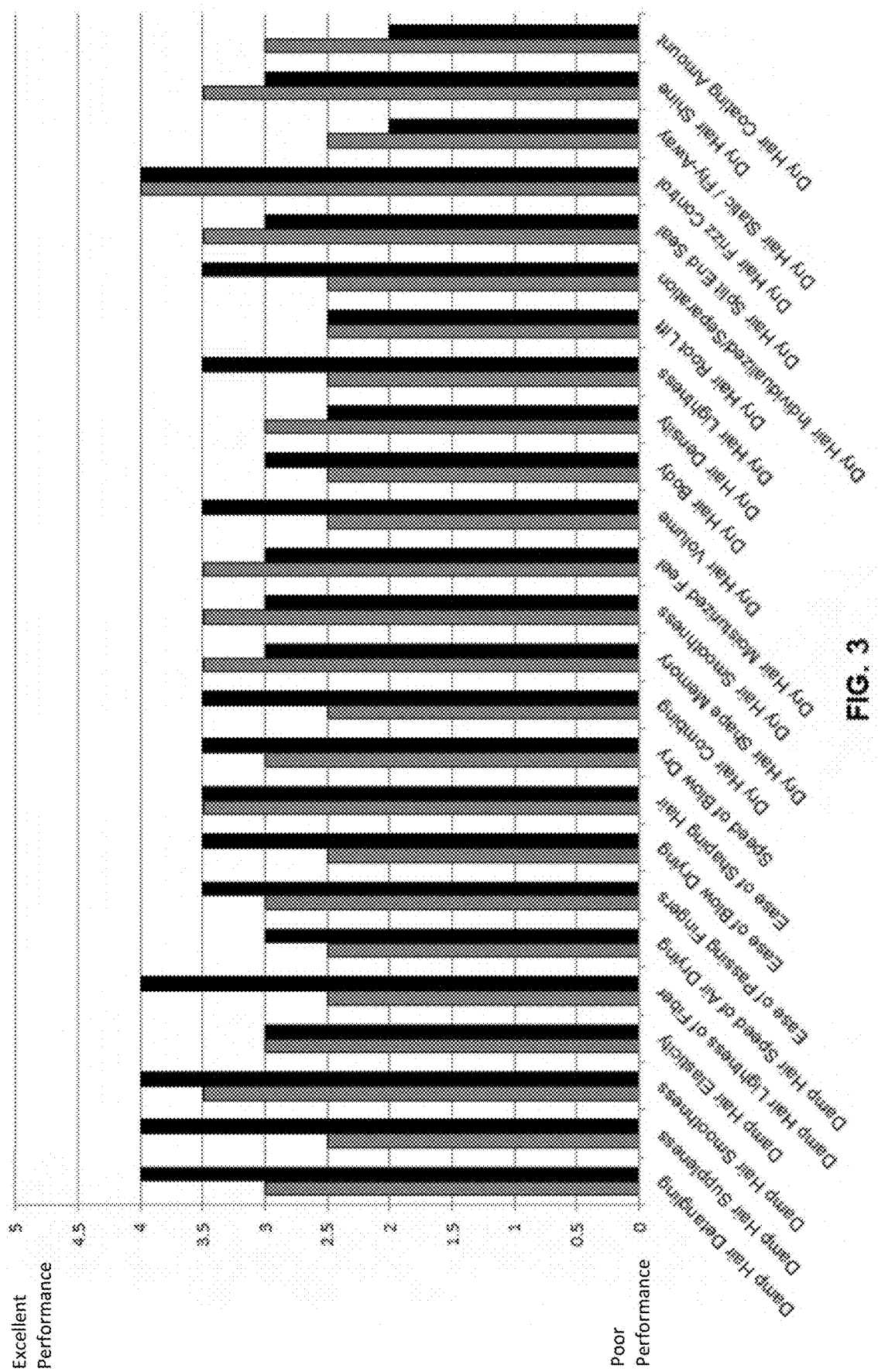
FIG. 3 is a bar graph comparing hair treated with a hair-treatment composition according to the instant disclosure (left bars, which are shaded), used as a post-shampoo treatment, with hair not treated with a hair-treatment composition according to the instant disclosure (right bars, which are solid).

Testing was carried out to determine the influence of Inventive Formulation #8 of Example 1 used as post-shampoo treatment. The entire head of hair of volunteers was first washed with a commercially available shampoo. After rinsing the shampoo from the hair, while the hair was still damp, half of the hair (half of the head of hair) was treated with Inventive Formulation #8. Inventive Formulation #8 was applied and allowed to remain on the hair for about 5 minutes before being rinsed from the hair. Both halves of the head of hair (the half treated with Inventive Formulation #8 and the half not treated with Inventive Formulation #8) were evaluated across a large number of cosmetic attributes. Each attribute was ranked on a scale from 0 to 5, where "0" represents "poor performance" and "5" represents "excellent performance." The results are presented in the graph provided in FIG. 3. The shaded bar on the left represents hair post-treated with Inventive Formulation #8; and the solid bar on the right represents the hair not post-treated with Inventive Formulation #8.

Inventive Formulation #8 was observed to work best as an interim treatment. Nonetheless, the data also show that hair treated with Inventive Formulation #8 as a post treatment was superior than no post treatment with respect to the dry hair attributes of hair shape memory, smoothness, and moisture feel, density, split end seal, static/fly-away, shine and coating amount, which are desirable attributes as a post-treatment. Root hair lift and frizz control were comparable to no post treatment and thus, not negatively impacted. The wet hair attributes did not rate as well for the invention but the dry hair attributes still provide an advantage.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

All percentages, parts and ratios herein are based upon the total weight of the compositions of the present invention, unless otherwise indicated.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or the fatty compound (the single fatty acid does not serve as both the emulsifier and the fatty component).

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat" (and its grammatical variations) as used herein also refers to contacting keratinous substrates such as hair with the compositions of the present disclosure.

A "rinse-off" product refers to a composition that is rinsed and/or washed from the hair with water either after or during the application of the composition onto the hair, and before drying and/or styling the hair. At least a portion of the composition is removed from the hair during the rinsing and/or washing.

A "leave-on" product refers to a composition that is not rinsed and/or washed from the hair after or during application of the composition onto the hair. The composition remains on the hair during drying and/or styling.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A hair-treatment composition comprising:
   (a) about 1 to about 3 wt. % of coconut oil;
   (b) about 2 to about 4 wt. % of one or more solid fatty alcohols;
   (c) about 0.1 to about 4 wt. % of one or more nonionic surfactants selected from esters of polyols with fatty acids or alkoxylated derivatives thereof;
   (d) about 0.1 to about 3 wt. % of 2-octyldodecanol;
   (e) about 1 to about 5 wt. % of brassicamidopropyl dimethylamine;
   (f) about 0.1 to about 3 wt. % of one or more acids selected from tartaric acid, salicylic acid, or mixtures thereof; and
   (g) 80 to 95 wt. % of water;
   wherein the composition is free of quaternary ammonium compounds and quaternary ammonium polymers, and
   all weight percentages are based on a total weight of the composition.

2. The hair-treatment composition of claim 1, wherein the one or more solid fatty alcohols are straight chain fatty alcohols selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, or mixtures thereof.

3. The hair-treatment composition of claim 2, wherein the one or more solid fatty alcohols are straight chain fatty alcohols selected from cetearyl alcohol, cetyl alcohol, stearyl alcohol, or mixtures thereof.

4. The hair-treatment composition of claim 1, wherein the one or more nonionic surfactants are selected from glyceryl distearate, glyceryl hydroxystearate, glyceryl laurate, glyceryl linoleate, glyceryl myristate, glyceryl oleate, glyceryl stearate, an alkoxylated derivate thereof, or mixtures thereof.

5. The hair-treatment composition of claim 1, wherein the composition includes both tartaric acid and salicylic acid.

6. A kit comprising:
   (a) a hair-treatment composition of claim 1;
   (b) a shampoo; and
   (c) a conditioner;
   wherein the hair-treatment composition, the shampoo, and the conditioner and separately contained.

7. A kit comprising:
   (a) a hair-treatment composition of claim 1; and
   (b) one or more chemical hair treatment compositions;
   wherein the hair-treatment composition and the one or more chemical treatment compositions are separately contained.

8. A hair-treatment composition comprising:
   (a) about 1 to about 3 wt. % of coconut oil;
   (b) about 2 to about 4 wt. % of one or more solid fatty alcohols;
   (c) about 0.1 to about 4 wt. % of one or more nonionic surfactants selected from glyceryl distearate, glyceryl hydroxystearate, glyceryl laurate, glyceryl linoleate, glyceryl myristate, glyceryl oleate, glyceryl stearate, an alkoxylated derivate thereof, or mixtures thereof;
(d) about 0.1 to about 3 wt. % of 2-octyldodecanol;
(e) about 1 to about 5 wt. % of brassicamidopropyl dimethylamine; and
(f) about 0.1 to about 3 wt. % of tartaric acid;
(g) about 80 to about 95 wt. % of water;
wherein the composition is free of quaternary ammonium compounds and quaternary ammonium polymers; and
all weight percentages are based on a total weight of the composition.

9. The hair-treatment composition of claim 8, wherein the one or more solid fatty alcohols are straight chain fatty alcohols selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol and 2-hexadecyl-1-eicosanol, or mixtures thereof.

10. The hair-treatment composition of claim 9, wherein the one or more solid fatty alcohols are straight chain fatty alcohols selected from cetearyl alcohol, cetyl alcohol, stearyl alcohol, or mixtures thereof.

11. A kit comprising:
(a) a hair-treatment composition of claim 8;
(b) a shampoo; and
(c) a conditioner;
wherein the hair-treatment composition, the shampoo, and the conditioner and separately contained.

12. A kit comprising:
(a) a hair-treatment composition of claim 8; and
(b) one or more chemical hair treatment compositions;
wherein the hair-treatment composition and the one or more chemical treatment compositions are separately contained.

13. A method for treating hair comprising applying to the hair a hair-treatment composition of claim 1 and optionally rinsing the hair-treatment composition from the hair.

14. The method of claim 13, wherein the method comprises:
imparting shine to the hair;
providing smoothness, softness, and/or discipline to the hair;
improving frizz control;
providing end seal of split ends; and/or
enhancing root lift.

15. A method for treating hair comprising applying to the hair a hair-treatment composition of claim 8 and optionally rinsing the hair-treatment composition from the hair.

16. The method of claim 15, wherein the method comprises:
imparting shine to the hair;
providing smoothness, softness, and/or discipline to the hair;
improving frizz control;
providing end seal of split ends; and/or
enhancing root lift.

* * * * *